(12) United States Patent
Lee et al.

(10) Patent No.: US 12,121,489 B2
(45) Date of Patent: *Oct. 22, 2024

(54) METHOD AND APPARATUS FOR CONTROLLING BALANCE

(71) Applicant: Samsung Electronics Co., Ltd., Suwon-si (KR)

(72) Inventors: Jusuk Lee, Hwaseong-si (KR); Kyung-Rock Kim, Yongin-si (KR); Keehong Seo, Seoul (KR); Bokman Lim, Yongin-si (KR); Jun-Won Jang, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 885 days.

This patent is subject to a terminal disclaimer.

(21) Appl. No.: 17/095,129

(22) Filed: Nov. 11, 2020

(65) Prior Publication Data

US 2021/0059889 A1 Mar. 4, 2021

Related U.S. Application Data

(63) Continuation of application No. 15/455,831, filed on Mar. 10, 2017, now Pat. No. 10,874,575.

(30) Foreign Application Priority Data

Nov. 2, 2016 (KR) .................. 10-2016-0144905

(51) Int. Cl.
*A61H 3/00* (2006.01)
*A61B 5/00* (2006.01)
(Continued)

(52) U.S. Cl.
CPC ............. *A61H 3/00* (2013.01); *A61B 5/1038* (2013.01); *A61B 5/1116* (2013.01);
(Continued)

(58) Field of Classification Search
CPC ................ A61H 3/00; A61H 2003/007; A61H 2201/164; A61H 2201/165;
(Continued)

(56) References Cited

U.S. PATENT DOCUMENTS 7,942,833 B2 5/2011 Yasuhara
8,075,449 B2 12/2011 Lee
(Continued)

FOREIGN PATENT DOCUMENTS

CN 1649698 A 8/2005
CN 101628415 A 1/2010
(Continued)

OTHER PUBLICATIONS

Chinese Office Action issued by the Chinese Patent Office on Dec. 31, 2020 for the corresponding CN Patent Application No. 201710372389.6.
(Continued)

*Primary Examiner* — Ariana Zimbouski
*Assistant Examiner* — Christine L Nelson
(74) *Attorney, Agent, or Firm* — Harness, Dickey & Pierce, P.L.C.

(57) ABSTRACT

A method and apparatus for helping a user walk may verify whether the user is in a standing state and calculate a torque that controls balance of the user, and an assistance force for controlling balance may be provided for the user based on the torque generated by an actuator.

20 Claims, 16 Drawing Sheets

(51) Int. Cl.
*A61B 5/103* (2006.01)
*A61B 5/11* (2006.01)
*A61F 2/68* (2006.01)
*A61F 2/70* (2006.01)
*A61F 2/50* (2006.01)
*A61H 1/02* (2006.01)

(52) U.S. Cl.
CPC .......... *A61B 5/4023* (2013.01); *A61B 5/4836* (2013.01); *A61B 5/746* (2013.01); *A61F 2/68* (2013.01); *A61F 2/70* (2013.01); *A61B 5/1036* (2013.01); *A61B 5/1121* (2013.01); *A61B 5/6831* (2013.01); *A61B 5/7455* (2013.01); *A61F 2002/5038* (2013.01); *A61H 1/0244* (2013.01); *A61H 2003/007* (2013.01); *A61H 2201/1215* (2013.01); *A61H 2201/1628* (2013.01); *A61H 2201/164* (2013.01); *A61H 2201/165* (2013.01); *A61H 2201/1671* (2013.01); *A61H 2201/5061* (2013.01); *A61H 2201/5069* (2013.01); *A61H 2201/5071* (2013.01); *A61H 2201/5084* (2013.01); *A61H 2205/088* (2013.01); *A61H 2205/106* (2013.01); *A61H 2230/625* (2013.01)

(58) Field of Classification Search
CPC . A61H 2201/5061; A61B 5/4836; A61F 2/70; A61F 2/68; A61F 2002/5038
See application file for complete search history.

(56) References Cited

U.S. PATENT DOCUMENTS

| | | | |
|---|---|---|---|
| 9,314,394 B2 | 4/2016 | Hirata et al. | |
| 10,874,575 B2 * | 12/2020 | Lee | A61B 5/4836 |
| 2010/0256537 A1 | 10/2010 | Menga | |
| 2011/0082566 A1 | 4/2011 | Herr et al. | |
| 2012/0172770 A1 | 7/2012 | Almesfer et al. | |
| 2013/0032413 A1 | 2/2013 | Smith et al. | |
| 2014/0260714 A1 | 9/2014 | Vallery et al. | |
| 2014/0296761 A1 | 10/2014 | Yamamoto et al. | |
| 2015/0088269 A1 | 3/2015 | Roh | |
| 2015/0196403 A1 | 7/2015 | Kim et al. | |
| 2015/0313786 A1 | 11/2015 | Sano | |

FOREIGN PATENT DOCUMENTS

| | | |
|---|---|---|
| CN | 102573746 A | 7/2012 |
| CN | 103263339 A | 8/2013 |
| CN | 104622669 A | 5/2015 |
| EP | 2896933 A1 | 7/2015 |
| JP | 2011-036375 A | 2/2011 |
| KR | 100731899 B1 | 6/2007 |
| KR | 10-0802533 B1 | 2/2008 |
| KR | 10-2012-0137229 | 12/2012 |
| KR | 101417895 B1 | 7/2014 |
| KR | 10-2016-0090088 | 7/2016 |
| WO | WO-2015/120186 A1 | 8/2015 |

OTHER PUBLICATIONS

J. Chiu and A. Goswami, "Design of a Wearable Scissored-Pair Control Moment Gyroscope (SP-CMG) for Human Balance Assist", Proceedings of the ASME 2014 International Design Engineering Technical Conferences and Computers and Information in Engineering Conference, IDETC/CIE 2014, Aug. 17-20, 2014, Buffalo, NY.

Lorenzo Chiari, et al., "Audio-Biofeedback for Balance Improvement: An Accelerometry-Based System", IEEE Transactions on Biomedical Engineering, vol. 52, No. 12, Dec. 2005, pp. 2108-2111.

A. Aruin and N. Rao, "Ankle-Foot Orthoses: Proprioceptive Inputs and Balance Implications", J Prosthet Orthot. Author manuscript; available in PMC Mar. 12, 2015, Published in final edited form as: J Prosthet Orthot. 2010; 22(4Suppl): 34-37.

M.N. Nyan et al. "A Wearable System for Pre-Impact Fall Detection". Journal of Biomechanics. Elsevier Ltd. 2008. p. 3475-3481.

Extended European Search Report issued on Dec. 4, 2017 for corresponding EP Application No. 17170473.7.

* cited by examiner

METHOD AND APPARATUS FOR CONTROLLING BALANCE

CROSS-REFERENCE TO RELATED APPLICATION

This application is a continuation application of U.S. application Ser. No. 15/455,831, filed on Mar. 10, 2017, which claims priority under 35 U.S.C. § 119 to Korean Patent Application No. 10-2016-0144905, filed on Nov. 2, 2016, in the Korean Intellectual Property Office, the entire contents of each of which are incorporated herein by reference in their entirety.

BACKGROUND

1. Field

At least one example embodiment relates to a method and/or apparatus for providing an assistance force for a user. For example at least one example embodiment relates to a method and/or apparatus for controlling balance of a user maintaining a standing posture.

2. Description of the Related Art

With the onset of rapidly aging societies, many people may experience inconvenience and/or pain from joint problems. Thus, there may be a growing interest in gait assistance apparatuses that may enable the elderly and/or patients having joint problems to walk with less effort. Furthermore, gait assistance apparatuses for intensifying muscular strength of human bodies may be useful for military purposes.

SUMMARY

Some example embodiments relate to a method of controlling balance of a user by a balance controlling apparatus.

In some example embodiments, the method includes measuring a balance state of the user; determining an assist mode of the balance control apparatus based on the balance state of the user; calculating a torque based on the assist mode; and instructing an actuator to provide the torque to balance the user.

In some example embodiments, the method further includes verifying whether the user is in a standing state, wherein the measuring measures the balance state, if the verifying verifies the user is in the standing state.

In some example embodiments, the verifying includes receiving data associated with the standing state, the data including at least one of a hip joint angle, a hip joint angular velocity, a hip joint angular acceleration, or inertial measurement unit (IMU) data; and verifying whether the user is in the standing state based on the data.

In some example embodiments, the measuring includes measuring the balance state based on a center of mass (COM) of the user.

In some example embodiments, the measuring based on the COM includes calculating the COM based on IMU data associated with the user and hip joint angle data, the hip joint angle data indicating a hip joint angle of the user; calculating a COM angle based on a difference between a desired posture and a posture associated with the COM; and calculating a COM angular velocity based on the COM angle.

In some example embodiments, the IMU data includes a pitch of an upper body of the user.

In some example embodiments, the measuring based on the COM includes receiving ankle joint angle data, the ankle joint angle data indicating an ankle joint angle of the user; calculating the COM based on the ankle joint angle; calculating a COM angle based on a difference between a desired posture and a posture associated with the COM; and calculating a COM angular velocity based on the COM angle.

In some example embodiments, the receiving the ankle joint angle data includes receiving the ankle joint angle data from an angle sensor, the angle sensor configured to attach to an ankle of the user.

In some example embodiments, the measuring includes measuring the balance state based on sole pressure data, the sole pressure data indicating a pressure applied to a sole of at least one foot of the user.

In some example embodiments, the measuring based on the sole pressure data includes receiving the sole pressure data from at least one pressure sensor, the at least one pressure sensor configured to measure pressure applied to the sole of the at least one foot of the user; and measuring the balance state based on the pressure.

In some example embodiments, the at least one pressure sensor includes a plurality of pressure sensors, and the measuring based on the sole pressure data includes measuring the balance state based on a change in the pressure measured by the plurality of pressure sensors.

In some example embodiments, the measuring includes measuring the balance state based on a zero moment point (ZMP) of the balance control apparatus.

In some example embodiments, the measuring based on the ZMP includes calculating the ZMP based on an acceleration of an inertial measuring unit (IMU); and measuring the balance state based on the ZMP.

In some example embodiments, the measuring of the balance state of the user includes calculating a COM of the user based on IMU data and hip joint angle data, the hip joint angle data indicating a hip joint angle of the user, calculating a COM angle based on a difference between a desired posture and a posture associated with the COM, and calculating a COM angular velocity based on the COM angle; and the determining the assist mode includes, comparing the COM angle with a plurality of threshold values to generate an angle result, comparing the COM angular velocity with the threshold values to generate an angular velocity result, and determining the assist mode from among a plurality of assist modes based on the angle result and the angular velocity result.

In some example embodiments, each of the assist modes corresponds to different COM angular velocities.

In some example embodiments, the calculating the torque includes determining a gain; and calculating the torque based on the gain, the COM angular velocity, the COM angle, and a desired angle.

In some example embodiments, the gain is adjustable based on at least one of a type of illness of the user, a physical condition of the user, or an assist method.

In some example embodiments, the measuring the balance state includes measuring a roll of an upper body of the user based on IMU data, and the determining the assist mode includes determining the assist mode to be a lateral assist mode, if the measured roll exceeds a threshold value.

In some example embodiments, the method further includes measuring a gait state of the user, the gait state being part of a gait cycle; calculating a gait assistance torque based on the gait state; and instructing the actuator to provide the gait assistance torque to the user to assist the user in completing the gait cycle.

Some example embodiments relate to a balance control apparatus.

In some example embodiments, the apparatus includes a processor configured to, receive sensing data from at least one sensor, measure a balance state of a user based on the sensing data, determine an assist mode based on the balance state, and calculate a torque based on the assist mode; and an actuator configured to generate the torque.

In some example embodiments, the actuator is an ankle actuator configured to connect to an ankle of the user, and the ankle actuator is configured to generate the torque.

In some example embodiments, the ankle actuator includes an angle sensor configured to measure an ankle joint angle of the user, and the processor is configured to measure the balance state based on the ankle joint angle.

Some example embodiments relate to a method of controlling balance of a user by a balance control apparatus.

In some example embodiments, the method includes verifying whether a user is in a standing state; measuring a balance state of the user, if the verifying verifies the user is in the standing state; determining an assist mode of the balance control apparatus based on the balance state; calculating an alarm torque based on the assist mode; and instructing an actuator to provide the alarm torque as feedback to the user.

Some example embodiments relate to a balance control apparatus.

In some example embodiments, the apparatus includes a processor configured to, receive sensing data from at least one sensor, verify whether a user is in a standing state based on the sensing data, measure a balance state of the user, if the processor verifies the user is in the standing state, determine an assist mode based on the balance state, and calculate an alarm torque based on the assist mode; and an actuator configured to generate the alarm torque.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
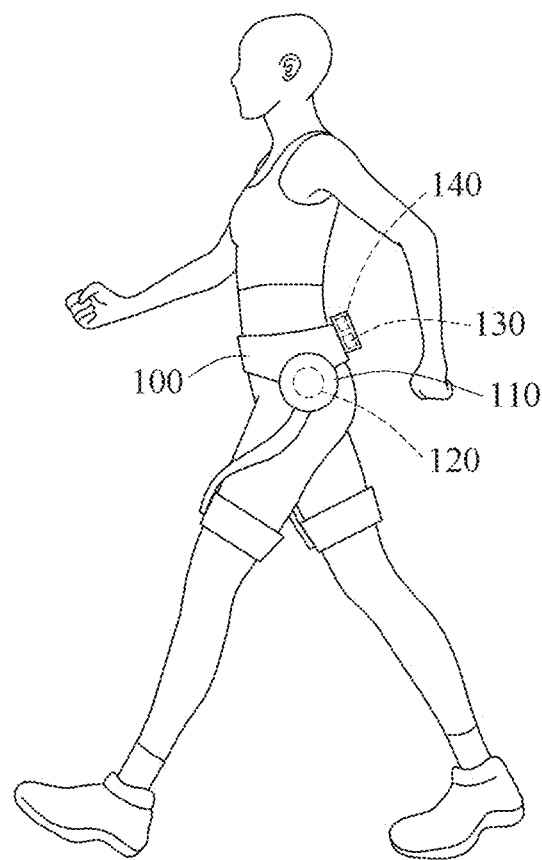
FIGS. 1 and 2 illustrate a gait assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

<Outline of Gait Assistance Apparatus>

Figure 2:
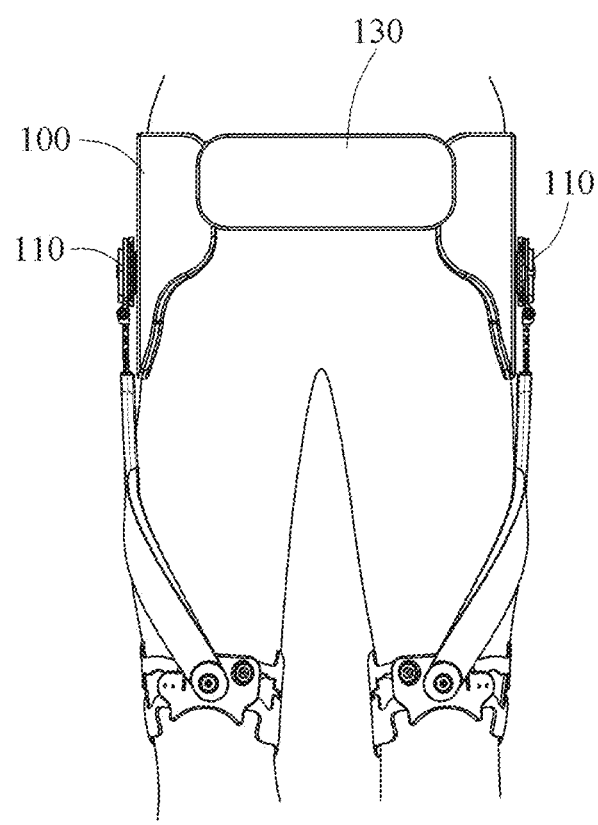

FIGS. 1 and 2 illustrate a gait assistance apparatus according to at least one example embodiment.

Referring to FIG. 1, a gait assistance apparatus 100 may be a device that is worn by a user and helps the user walk. FIG. 1 illustrates an example of a hip-type gait assistance apparatus, however, a type of walking assistance apparatus is not limited to the hip-type gait assistance apparatus. Accordingly, the gait assistance apparatus 100 may be, for example, one or more of a gait assistance apparatus for supporting a portion of a pelvic limb, a gait assistance apparatus for supporting up to a knee, and a gait assistance apparatus for supporting up to an ankle, and a gait assistance apparatus for supporting an entire pelvic limb.

Referring to FIGS. 1 and 2, the gait assistance apparatus 100 includes an actuator 110, a sensor 120, an inertial measurement unit (IMU) 130, and a controller 140.

The actuator 110 provides an assistance force for a hip joint of a user. For example, the actuator 110 may be located on, for example, a right hip portion and/or a left hip portion of the user. The actuator 110 may include a motor to generate a rotational torque.

The sensor 120 measures a hip joint angle of the user while the user is ambulatory. Information on the hip joint angle sensed by the sensor 120 may include an angle of a right hip joint, an angle of a left hip joint, a difference between both hip joint angles, and/or a direction of motion for a hip joint. For example, the sensor 120 may be located in the actuator 110. The sensor 120 may include a potentiometer. The potentiometer may sense a right (R)-axis joint angle, a left (L)-axis joint angle, an R-axis joint angular velocity, and/or an L-axis joint angular velocity, based on a gait motion of the user.

The IMU 130 measures acceleration information and/or posture information while the user is ambulatory. For example, the IMU 130 senses an x-axis acceleration, a y-axis acceleration, a z-axis acceleration, an x-axis angular velocity, a y-axis angular velocity, and a z-axis angular velocity, based on a gait motion of the user. The gait assistance apparatus 100 may detect a point at which a foot of the user lands based on the acceleration information measured by the IMU 130.

The gait assistance apparatus 100 may include, in addition to the above-described sensor 120 and the IMU 130, another sensor (for example, an electromyography (EMG) sensor) configured to sense a change in a biosignal or a quantity of motion of a user based on a gait motion.

The controller 140 may control the actuator 110 to output an assistance force to help the user walk. For example, the controller 140 may output a control signal to control the actuator 110 to generate a torque. The actuator 140 may generate the torque based on the control signal output by the controller 140. The torque may be set by an external device or the controller 140.

The above-described gait assistance apparatus 100 may provide an additional function of determining a moving state of the user, in addition to a function of helping the user walk. For example, the gait assistance apparatus 100 may perform a function of helping a user control balance. For example, the gait assistance apparatus 100 may help the user maintain a standing posture. Description of a method by which the gait assistance apparatus 100 helps the user control balance will be provided with reference to FIGS. 3 through 18.

<Outline of Method of Controlling Balance>

Figure 3:
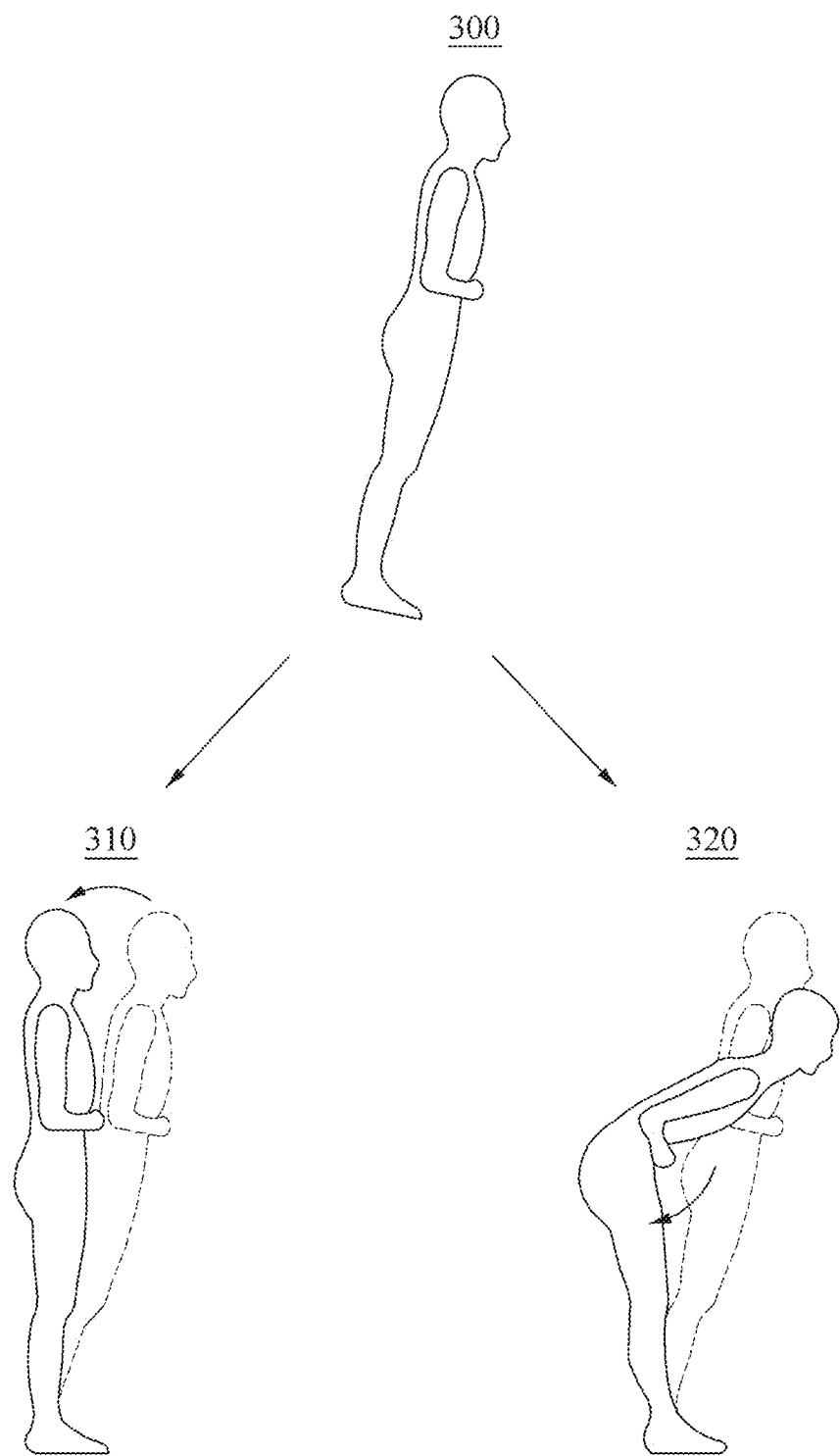
FIG. 3 illustrates balancing methods related to an external force according to at least one example embodiment.

FIG. 3 illustrates balancing methods related to an external force according to at least one example embodiment.

Referring to FIG. 3, in a case 300 in which an external force is applied to a person from behind the person, the person may lean a body forward. A mechanism for helping a person recover balance may be different depending on a magnitude of the applied external force.

In a first case 310 in which a relatively weak external force is applied, the person may recover balance by leaning an upper body backward using hamstrings (HAM) and lumbar paraspinal muscles (PAR) around a lumbar spine.

In a second case 320 in which a relatively strong external force is applied, the person may recover balance by moving a hip backward and leaning the upper body forward by primarily using quadriceps (QUAD) and abdominal muscles (ABD). Subsequently, the person may stand by raising the upper body up.

Balance may be lost because an external force is applied or senses are uncontrolled due to a damaged sensory organ. For example, patients having damaged muscles or damaged nerves may be unable to maintain balance on their own.

A neuromuscular disease may cause amyotrophia and a weakness in a lower body muscular strength due to a damaged peripheral nervous system which causes gait difficulty. The neuromuscular disease may include multiple sclerosis, Charcot-Marie-Tooth (CMT) disease, and Guillain-Barre syndrome. CMT disease may cause defects in peripheral motor nerves and sensory nerves which may cause foot drop difficulty, and may cause a loss of sensation, a muscular atrophy, a muscle weakness in a hand, an arm, a foot, and a leg. Thus, a patient having CMT disease may have difficulty walking, standing, or grabbing an object.

Maintaining a standing posture may be relatively easy for a normal person (non-disabled person), but may be relatively difficult for a patient with the neuromuscular disease. Various senses, for example, a proprioceptive reflex, a visual system, and a vestibular system, are used to maintain the standing posture. However, the patient may be unable to sense a minute motion for maintaining balance because the sense of the proprioceptive reflex of an ankle is lost due to a neural damage. The patient may experience difficulty in maintaining balance because a muscular strength that bears an external force is weakened when an amount of lower body muscles is reduced.

Figure 4:
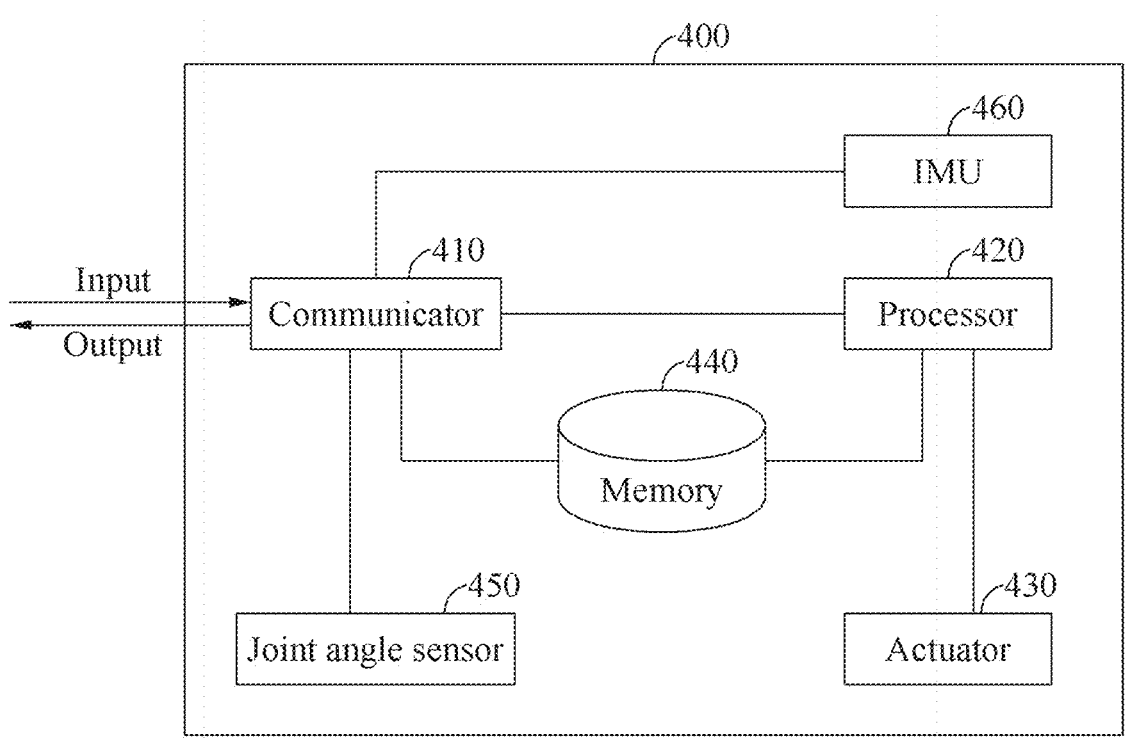
FIG. 4 is a block diagram illustrating a balance controlling apparatus according to at least one example embodiment.

FIG. 4 is a block diagram illustrating a balance controlling apparatus according to at least one example embodiment.

Referring to FIG. 4, a balance controlling apparatus 400 may correspond to the above-described gait assistance apparatus 100 illustrated in FIGS. 1 and 2. For example, the balance controlling apparatus 400 may include a function of assisting a gait of a user, in addition to a function of controlling balance of the user.

The balance controlling apparatus 400 may include a communicator 410, a processor 420, an actuator 430, a memory 440, a joint angle sensor 450, and an inertial measurement unit (IMU) 460.

The communicator 410 may be connected to the processor 420, the memory 440, the joint angle sensor 450, and the IMU 460, and may transmit and receive data. The communicator 410 may be connected to an external device, and may transmit and receive data. The communicator 410 may be implemented as circuitry in the balance controlling apparatus 400. For example, the communicator 410 may include an internal bus and an external bus. In another example, the communicator 410 may be an element configured to connect the balance controlling apparatus 400 and the external device. The communicator 410 may be an interface. The communicator 410 may receive data from the external device and transmit the data to the processor 420 and the memory 440.

The processor 420 may process data received by the communicator 410 and data stored in the memory 440. The processor 420 may transmit or input information on a torque to the actuator 430. The processor 420 may correspond to the above-described controller 140.

A "processor" may be a data processing device implemented as hardware including a circuit having a physical structure for executing desired operations. For example, the desired operations may involve a code and instructions included in a program. For example, the data processing device implemented as hardware may include one or more of a microprocessor, a central processing unit (CPU), a processor core, a multi-core processor, a multiprocessor, an application-specific integrated circuit (ASIC), and a field programmable gate array (FPGA).

The processor 420 may execute a code, for example, software, stored in a memory, for example, the memory 440, and to be read by a computer, and instructions caused by the processor 420.

The actuator 430 may operate based on the information on the torque. The actuator 430 may generate an assistance force through a rotation of a motor. The actuator 430 may correspond to the above-described actuator 110 of FIG. 1.

The memory 440 may store the data received by the communicator 410 and the data processed by the processor 420. For example, the memory 440 stores a program.

In an example, the memory 440 includes a random access memory (RAM), a flash memory, a hard disk drive, an optical disk drive, and at least one of a volatile memory or a non-volatile memory.

The memory 440 stores an instruction set, for example, software, to operate the balance controlling apparatus 400. The instruction set to operate the balance controlling apparatus 400 is executed by the processor 420.

The joint angle sensor 450 measures an angle of a joint of the user. For example, the joint of the user includes a hip joint, a knee joint, and an ankle joint. The joint angle sensor 450 may measure an angular velocity of the hip joint, an angular velocity of the knee joint, and an angular velocity of the ankle joint.

The IMU 460 measures a change in an orientation of the balance controlling apparatus 400. For example, the IMU 460 measures a direction of a torso of the user wearing the balance controlling apparatus 400.

Detailed description of the functions performed by the communicator 410, the processor 420, the actuator 430, the memory 440, the joint angle sensor 450, and the IMU 460 will be provided with reference to FIGS. 5 through 18.

Figure 5:
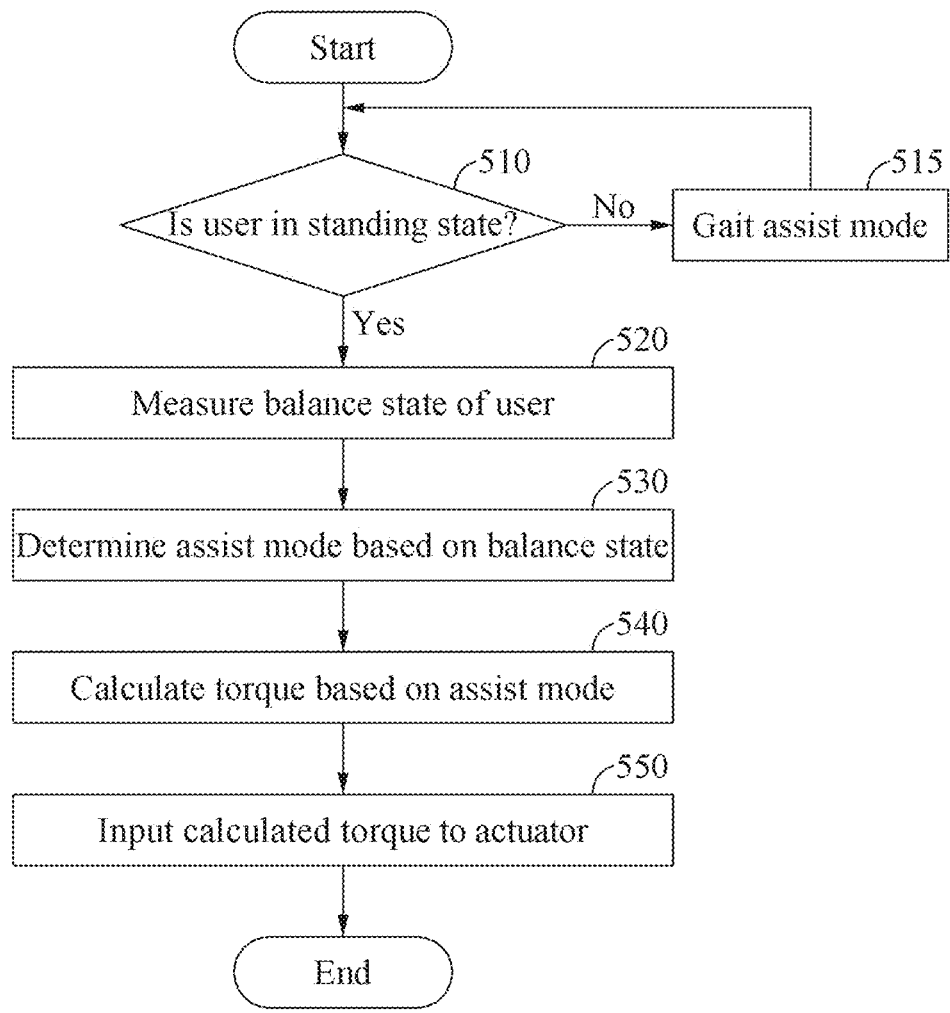
FIG. 5 is a flowchart illustrating a method of controlling balance according to at least one example embodiment.

FIG. 5 is a flowchart illustrating a method of controlling balance according to at least one example embodiment.

Referring to FIG. 5, in operation 510, the processor 420 verifies whether a user wearing the balance controlling apparatus 400 is in a standing state. Detailed description of a method of verifying whether the user is in the standing state will be provided with reference to FIG. 6. If the processor 420 verifies that the user is not in the standing state, the processor 420 may perform operation 515. In contrast, if the processor 420 verifies that the user is in the standing state, the processor 420 may perform operation 520.

In operation 515, the processor 420 sets an operational mode of the balance controlling apparatus 400 to be a gait assist mode. Detailed description of the gait assist mode will be provided with reference to FIG. 17.

In operation 520, the processor 420 measures a balance state of the user. The balance state of the user may indicate a magnitude of an external force applied to the user. The balance state may include at least one of a center of mass (COM), a COM angle, a COM angular velocity, a hip joint angle, or an ankle joint angle of the user. Detailed description of a method of measuring the balance state of the user will be provided with reference to FIGS. 7 through 14.

In operation 530, the processor determines an assist mode based on the balance state. For example, the processor 420 determines the assist mode corresponding to the measured balance state among a plurality of preset assist modes. Detailed description of a method of determining the assist mode corresponding to the measured balance state will be provided with reference to FIG. 15.

In operation 540, the processor 420 calculates a torque based on the determined assist mode. For example, a method of calculating a torque may be different depending on an assist mode. Detailed description of a method of calculating the torque will be provided with reference to FIG. 16.

In operation 550, the processor 420 inputs the calculated torque to the actuator 430. For example, the processor 420 inputs, to the actuator 430, a value of a current or a value of a voltage each corresponding to the calculated torque. The actuator 430 may operate based on the input torque.

While not illustrated, in some example embodiments, in some example embodiments, the balance controlling apparatus 400 may utilize the verification that the user is standing in operation 510 in an attempt to avoid problems associated with prolonged standing. These problems may include the appearance of varicose veins, cardiovascular disorders such as carotid atherosclerosis, joint compression, muscle fatigue and/or syncope, also known as fainting.

For example, after determining that the user is standing in operation 510, the processor 420 may start a timer to track a length of time the user is standing and after a desired (or, alternatively, a preset) time, the processor 420 may provide the user with feedback indicating that the user has been standing for an excess period of time. Alternatively, in some example embodiments, the processor 420 may disable the assistance torque provided, in operation 550, to assist the user with maintaining a standing posture after the expiration of time.

Figure 6:
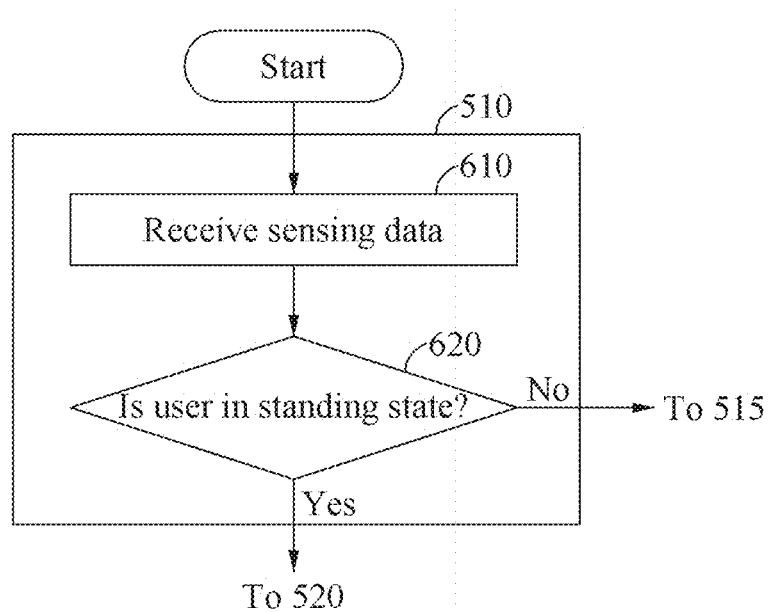
FIG. 6 is a flowchart illustrating a method of verifying whether a user is in a standing state according to at least one example embodiment.

FIG. 6 is a flowchart illustrating a method of verifying whether a user is in a standing state according to at least one example embodiment.

Referring to FIG. 6, operation 510 described with reference to FIG. 5 may include operations 610 and 620.

In operation 610, the communicator 410 receives sensing data from at least one sensor. The sensing data includes at least one of a hip joint angle, a hip joint angular velocity, a hip joint angular acceleration, a knee joint angle, a knee joint angular velocity, a knee joint angular acceleration, an ankle joint angle, an ankle angular velocity, an ankle angular acceleration, or inertial measurement unit (IMU) data. At least one of sensors may include the joint angle sensor 450 and the IMU 460. The joint angle sensor 450 may include a hip joint angle sensor, a knee joint angle sensor, or an ankle joint angle sensor.

The communicator 410 may be wirelessly connected to the knee joint angle sensor and the ankle joint angle sensor. For example, the communicator 410 may exchange data with the knee joint angle sensor and the ankle joint angle sensor through Bluetooth.

In operation 620, the processor 420 verifies whether the user is in the standing state based on the received sensing data. The processor 420 verifies whether the user is in the standing state based on at least one of the hip joint angle, the hip joint angular velocity, the hip joint angular acceleration, the knee joint angle, the knee joint angular velocity, the knee joint angular acceleration, the ankle joint angle, the ankle angular velocity, the ankle angular acceleration, or the IMU data. For example, the processor 420 verifies that the user is in the standing state when the sensing data is maintained within a desired (or, alternatively, a preset) range during a desired (or, alternatively, a preset) period of time.

Figure 7:
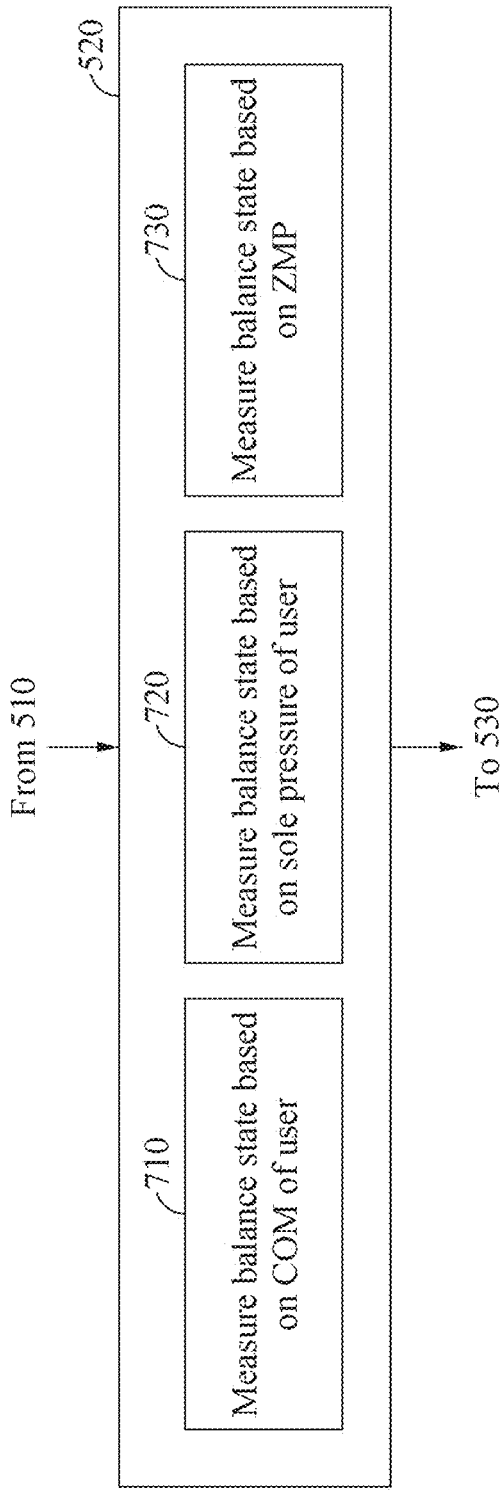
FIG. 7 is a flowchart illustrating a method of measuring a balance state of a user according to at least one example embodiment.

FIG. 7 is a flowchart illustrating a method of measuring a balance state of a user according to at least one example embodiment.

Referring to FIG. 7, operation 520 of measuring a balance state based on COM, described with reference to FIG. 5, may include at least one of operations 710, 720, or 730.

Operations 710, 720, and 730 may be performed in parallel, and at least one of operations 710, 720, or 730 may be complexly performed. For example, a weight is assigned to a balance state calculated in each operation.

In operation 710, the processor 420 measures the balance state based on a center of mass (COM) of the user. Detailed description of a method of measuring the balance state based on the COM will be provided with reference to FIGS. 8 through 11.

In operation 720, the processor 420 measures the balance state based on a sole pressure that is a pressure on a sole of the user. For example, the processor 420 measures the balance state by determining a center of pressure to be applied to the sole. Detailed description of a method of measuring the balance state based on the sole pressure will be provided with reference to FIGS. 12 and 13.

In operation 730, the processor 420 measures the balance state based on a zero moment point (ZMP) of the balance controlling apparatus 400. Detailed description of a method of measuring the balance state based on the ZMP will be provided with reference to FIG. 14.

Figure 8:
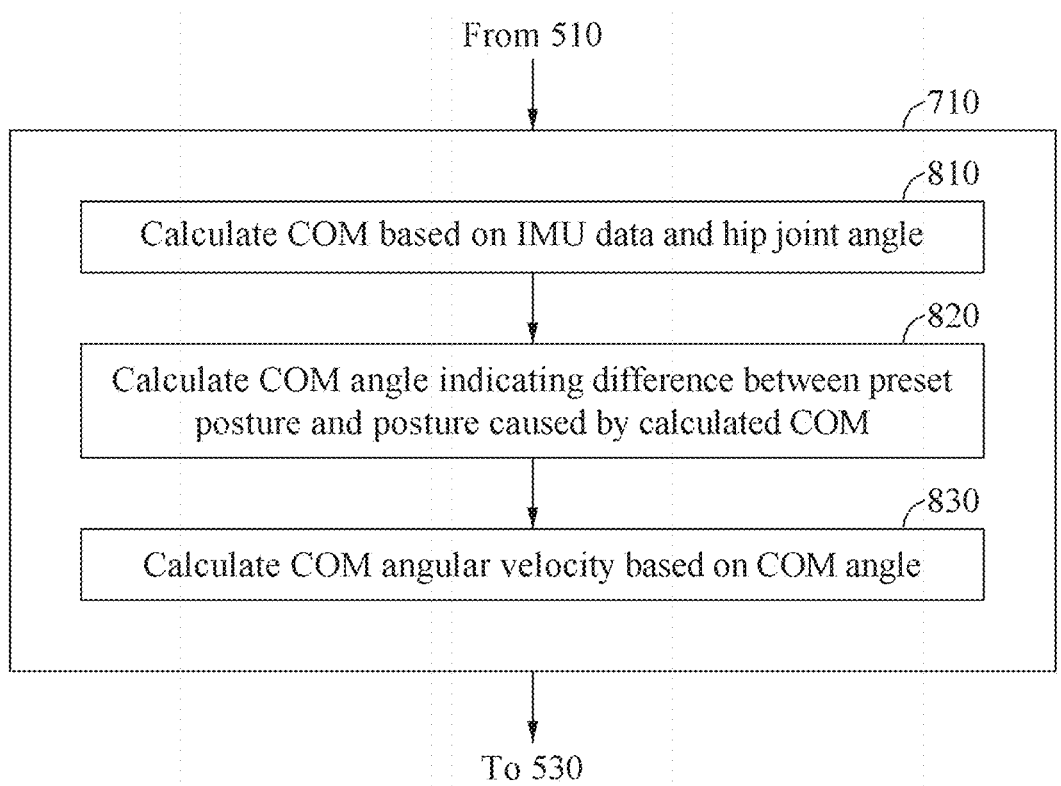
FIG. 8 is a flowchart illustrating a method of measuring a balance state based on a center of mass (COM) of a user according to at least one example embodiment.

FIG. 8 is a flowchart illustrating a method of measuring a balance state based on a center of mass (COM) of a user according to at least one example embodiment.

Referring to FIG. 8, operation 710, of measuring balance state based on the COM, described with reference to FIG. 7, may include operations 810, 820, and 830.

Operations 810, 820, and 830 may be performed in response to the balance controlling apparatus 400 being unable to sense or obtain an ankle joint angle. Before operation 810 is performed, inertial measurement unit (IMU) data and a hip joint angle may be obtained.

In operation 810, the processor 420 calculates the COM of the user based on the IMU data and the hip joint angle. The IMU data includes at least one of a roll or a pitch of an upper body of the user, and the processor 420 measures at least one of the roll or the pitch of the upper body of the user based on the IMU data. For example, the processor 420 models a state of the user and calculates the COM based on the modeled state of the user. Detailed description of a method of calculating the COM based on the modeled state will be provided with reference to FIG. 9.

In operation 820, the processor 420 calculates a COM angle indicating a difference between a desired (or, alternatively, a preset) posture and a posture caused by the calculated COM. The desired (or, alternatively, the preset) posture may be a posture in which a straight line formed by a heel of the user and the COM is identical to a gravitational direction. Detailed description of the COM angle will be provided with reference to FIG. 10.

In operation 830, the processor 420 calculates a COM angular velocity based on the COM angle. For example, the processor 420 calculates the COM angle at a desired (or, alternatively, a predetermined) time interval and calculates the COM angular velocity using the calculated COM angle. The balance state may include the calculated COM, the calculated COM angle, and the calculated COM angular velocity.

Figure 9:
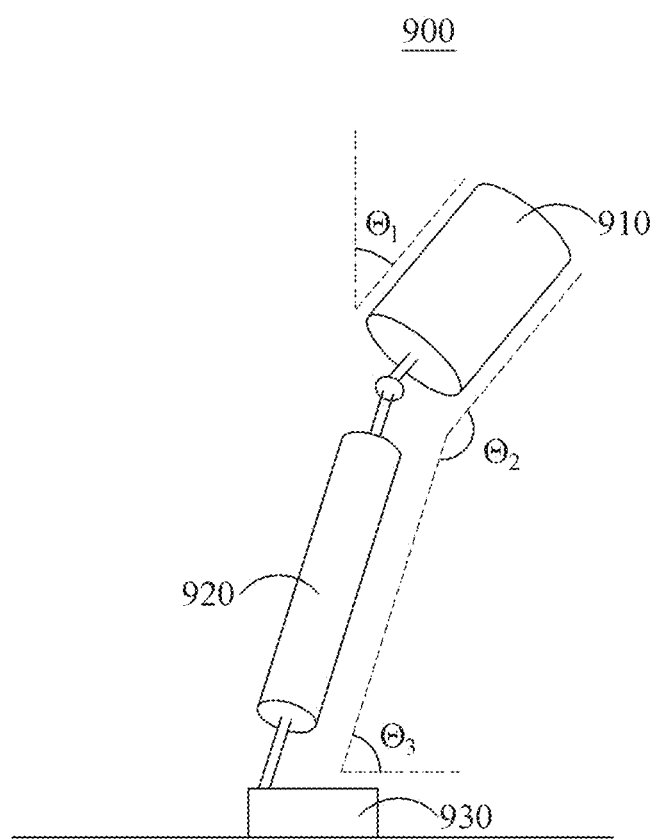
FIG. 9 illustrates a mechanically modeled state of a user according to at least one example embodiment.

FIG. 9 illustrates a mechanically modeled state of a user according to at least one example embodiment.

Referring to FIG. 9, a state of a user to which an external force is applied may be modeled.

The processor 420 models the state of the user based on inertial measurement unit (IMU) data and a hip joint angle. For example, body information of the user may be stored in advance. The body information may include a height, a length of an upper body, a length of a lower body, a body weight, a weight of the upper body, and a weight of the lower body of the user. The modeled state of the user may be divided into an upper body portion 910 and a lower body portion 920 based on a hip joint. The modeled state of the user may be divided into the lower body portion 920 and a leg portion 930 based on an ankle joint. The upper body portion 910 may include a head, an arm, and a torso of the user. The lower body portion 920 may include a thigh and a calf, and a knee joint of the user and the knee joint may be assumed to be stretched.

The processor 420 estimates an ankle joint angle $\theta_3$ based on the IMU data indicating a pitch $\theta_1$ of the upper body and a hip joint angle $\theta_2$. The processor 420 models the state of the user based on the pitch $\theta_1$ of the upper body, the hip joint angle $\theta_2$, and the ankle joint angle $\theta_3$. The processor 420 calculates a center of mass (COM) of the user based on the modeled state of the user.

Figure 10:
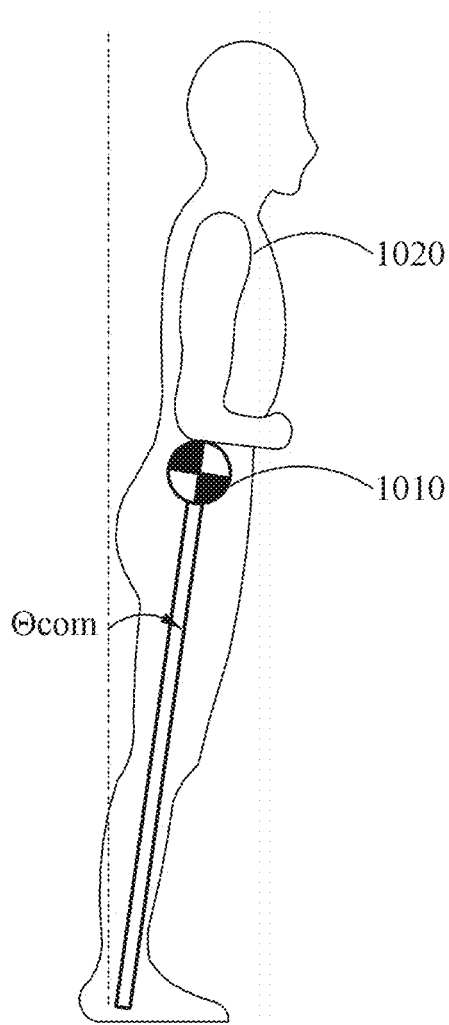
FIG. 10 illustrates a calculated center of mass (COM) of a user according to at least one example embodiment.

FIG. 10 illustrates a calculated center of mass (COM) of a user according to at least one example embodiment.

Referring to FIG. 10, a center of mass (COM) 1010 calculated in operation 810 described with reference to FIGS. 8 and 9 exists inside of a body of the user. The processor 420 determines a current posture 1020 of the user based on the COM 1010.

The processor 420 calculates a COM angle $\theta_{com}$ indicating a difference between a preset posture and the posture 1020 caused by the COM 1010. The preset posture may be a posture in which a straight line formed by a heel of the user and a COM is identical to a gravitational direction.

Figure 11:
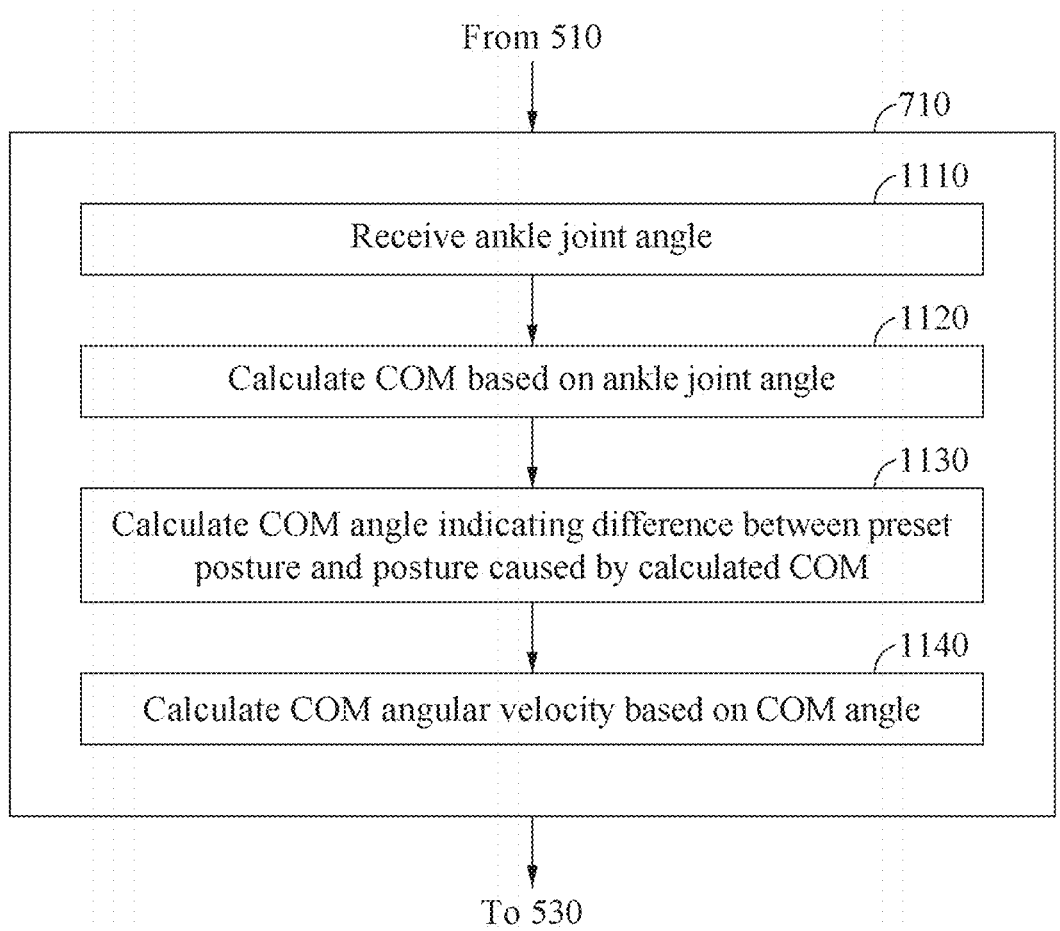
FIG. 11 is a flowchart illustrating a method of measuring a balance state based on a center of mass (COM) of a user according to at least one example embodiment.

FIG. 11 is a flowchart illustrating a method of measuring a balance state based on a center of mass (COM) of a user according to at least one example embodiment.

Operation 710 described with reference to FIG. 7 may include operations 1110, 1120, 1130, and 1140. Operations 1110, 1120, 1130, and 1140 may be performed in response to the balance controlling apparatus 400 sensing or obtaining an ankle joint angle.

In operation 1110, the communicator 410 receives the ankle joint angle. For example, the communicator 410 receives the ankle joint angle from an ankle joint angle sensor. The ankle joint angle sensor may use a resistance method, a capacitance method, and/or a polarized method.

In operation 1120, the processor 420 calculates the COM based on the ankle joint angle. For example, the processor 420 models a state of the user and calculates the COM based on the modeled state of the user. Repeated description of the method of modeling the state of the user will be omitted for increased clarity and conciseness because the descriptions provided with reference to FIG. 9 are also applicable to FIG. 11.

In operation 1130, the processor 420 calculates a COM angle indicating a difference between a desired (or, alternatively, a preset) posture and a posture caused by the calculated COM. Detailed description of operation 1130 is omitted for increased clarity and conciseness because it is essentially the same as the description of operation 820 of FIG. 8.

In operation 1140, the processor 420 calculates a COM angular velocity based on the COM angle. Detailed description of operation 1140 is omitted for increased clarity and conciseness because it is essentially the same as the description of operation 830 of FIG. 8.

Figure 12:
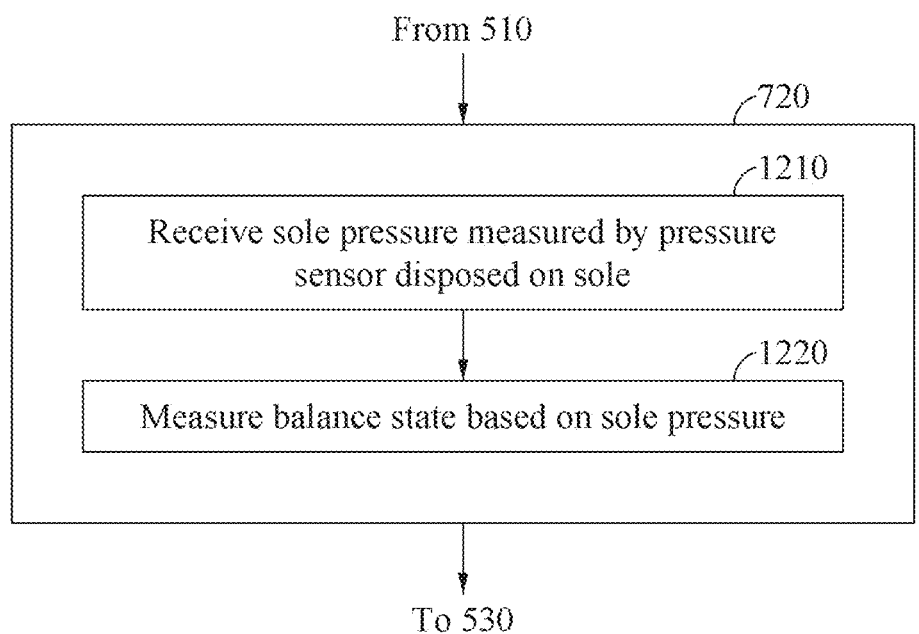
FIG. 12 is a flowchart illustrating a method of measuring a balance state based on a sole pressure that is a pressure on a sole of a user according to at least one example embodiment.

FIG. 12 is a flowchart illustrating a method of measuring a balance state based on a sole pressure that is a pressure on a sole of a user according to at least one example embodiment.

Referring to FIG. 12, operation 720 of measuring the balance state based on sole pressure, described with reference to FIG. 7, may include operations 1210 and 1220.

In operation 1210, the communicator 410 receives, from a pressure sensor disposed on a sole, a sole pressure measured by the pressure sensor. For example, a plurality of pressure sensors is disposed on an insole of a shoe. Detailed description of the pressure sensors disposed on the insole will be provided with reference to FIG. 13.

In operation 1220, the processor 420 measures the balance state based on the sole pressure. For example, the processor 420 calculates a center of pressure (COP) based on the sole pressure. The COP may be calculated such that the COP is located on the sole of the user. The balance state of the user may be measured based on the calculated COP. For example, if the COP is located towards a front of the sole, the user may be tilted forward.

A center of mass (COM) angle corresponding to a position of the COP may be set in advance. For example, a matching table for the position of the COP and the COM angle may be stored in the memory 440 in advance. The processor 420 may determine the COM angle corresponding to the position of the calculated COP. The processor 420 calculates a COM angular velocity based on the COM angle.

Figure 13:
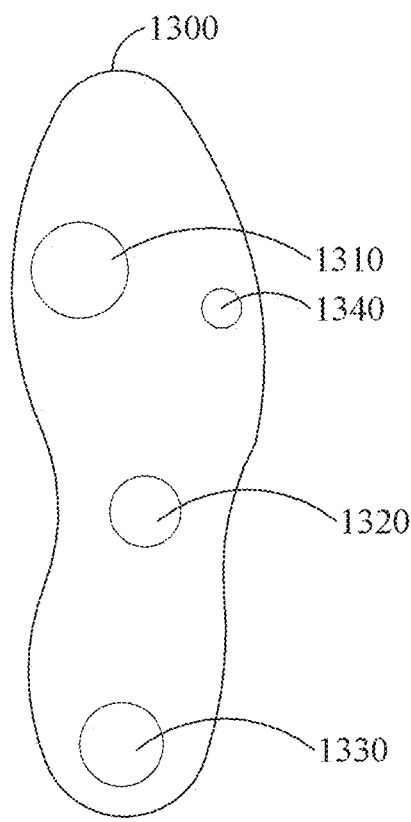
FIG. 13 illustrates a method of measuring a sole pressure of a user according to at least one example embodiment.

FIG. 13 illustrates a method of measuring a sole pressure of a user according to at least one example embodiment.

Referring to FIG. 13, a plurality of pressure sensors 1310, 1320, 1330, and 1340 is included in an insole 1300. Each pressure sensor may measure a magnitude of a pressure applied to each pressure sensor. Each pressure sensor may measure a pressure at a desired (or, alternatively, a preset) time interval. The pressure sensors 1310, 1320, 1330, and 1340 may be located at major portions of the insole 1300 that press against the sole of the user. For example, pressure sensors are disposed on a heel or a ball of a sole.

Each of the pressure sensors 1310, 1320, 1330, and 1340 may transmit the measured pressure to the communicator 410 through wireless communication. The processor 420 measures a change in pressure.

Figure 14:
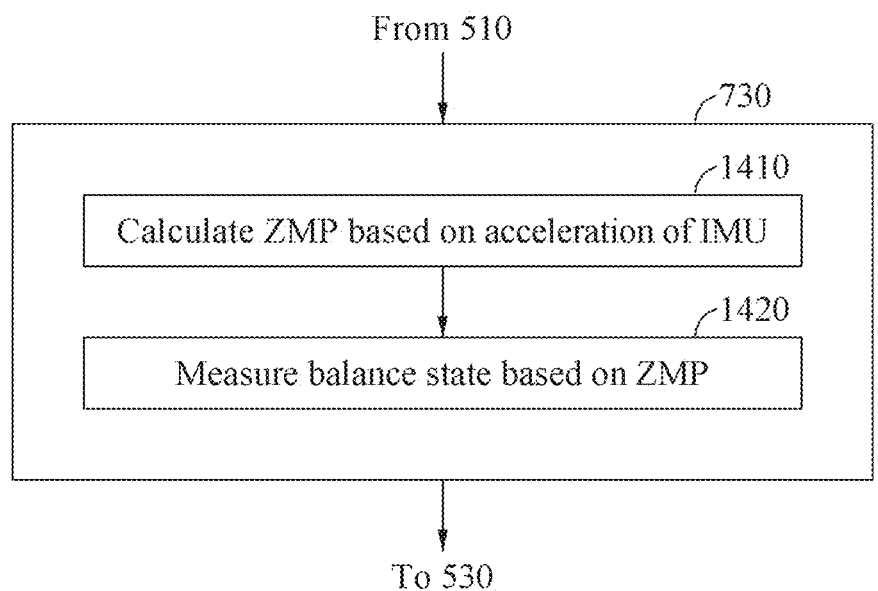
FIG. 14 is a flowchart illustrating a method of measuring a balance state based on a zero moment point (ZMP) according to at least one example embodiment.

FIG. 14 is a flowchart illustrating a method of measuring a balance state based on a zero moment point (ZMP) according to at least one example embodiment.

Referring to FIG. 14, operation 730 of measuring the balance state based on ZMP, described with reference to FIG. 7, may include operations 1410 and 1420.

In operation 1410, the processor 420 calculates the ZMP based on inertial measurement unit (IMU) data. The IMU data may include an acceleration of the IMU 460.

The ZMP may be a point with respect to which dynamic reaction force at the contact of the foot of the user with the ground does not produce any moment in the horizontal direction, i.e. the point where the total of horizontal inertia and gravity forces equals zero.

In operation 1420, the processor 420 measures a balance state based on the ZMP.

Figure 15:
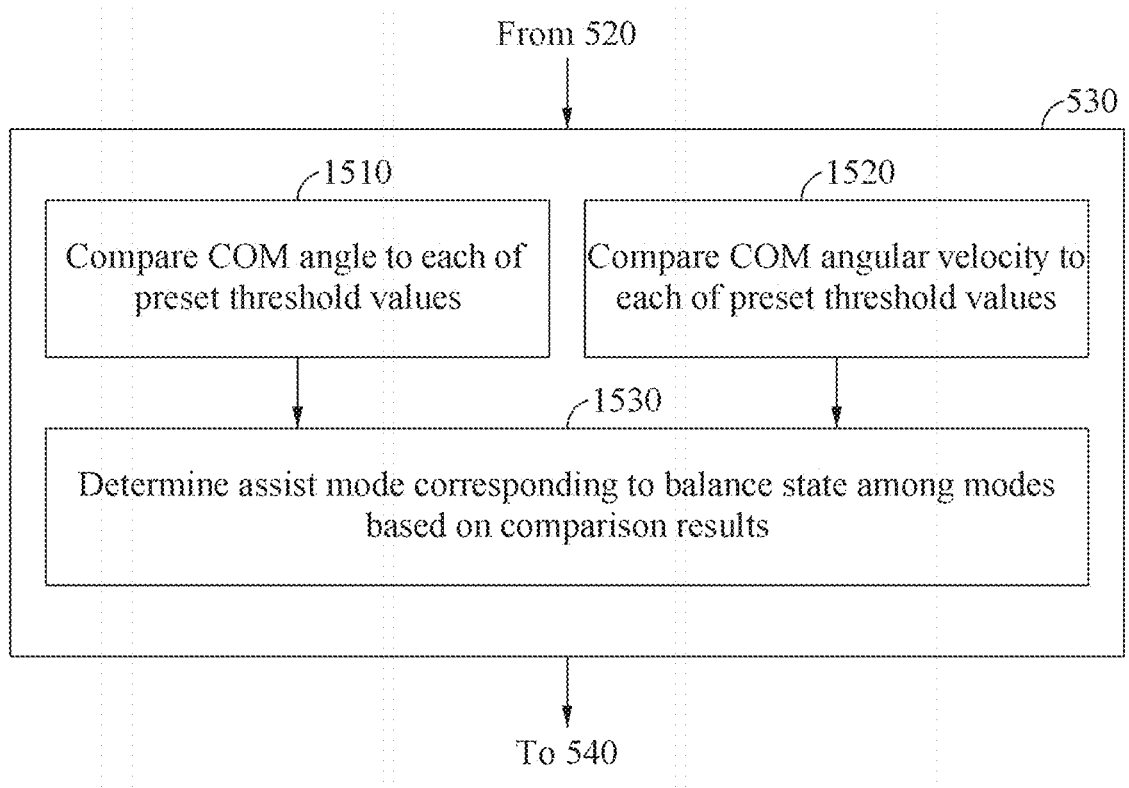
FIG. 15 is a flowchart illustrating a method of determining an assist mode corresponding to a balance state according to at least one example embodiment.

FIG. 15 is a flowchart illustrating a method of determining an assist mode corresponding to a balance state according to at least one example embodiment.

Referring to FIG. 15, operation 530 of determining the assistance mode, described with reference to FIG. 5, may include operations 1510, 1520, and 1530. Operations 1510 and 1520 may be performed in parallel.

In operation 1510, the processor 420 compares a calculated center of mass (COM) to each of a plurality of desired (or, alternatively, preset threshold values. For example, the processor 420 may compare A COM angle to each of the threshold values using Equations 1 and 2. A first threshold value may be less than a fourth threshold value. A range of the first threshold value and the second threshold value may partially overlap a range of a third threshold value and a fourth threshold value.

$$\text{First threshold value} < |\text{COM angle}| < \text{Second threshold value} \quad [\text{Equation 1}]$$

$$\text{Third threshold value} < |\text{COM angle}| < \text{Fourth threshold value} \quad [\text{Equation 2}]$$

In operation 1520, the processor 420 compares a calculated COM angular velocity to each of the desired (or, alternatively, the preset) threshold values. For example, the processor 420 may compare the COM angular velocity to each of the threshold values using Equations 3 and 4. A fifth threshold value may be less than a seventh threshold value.

$$|\text{COM angular velocity}| < \text{Fifth threshold value} \quad [\text{Equation 3}]$$

$$\text{Sixth threshold value} < |\text{COM angular velocity}| < \text{Seventh threshold value} \quad [\text{Equation 4}]$$

In operation 1530, the processor 420 may determine an assist mode corresponding to the balance state based on a comparison of results in operations 1510 and 1520. For example, the processor 420 determines the assist mode corresponding to the balance state among a plurality of assist modes.

For example, when Equations 1 and 3 are simultaneously satisfied, the processor 420 may determine the assist mode to be a first assist mode. When Equations 2 and 4 are simultaneously satisfied, the processor 420 may determine the assist mode to be a second assist mode. When the balance state is not determined to correspond to the first assist mode and the second assist mode, the processor 420 may determine the assist mode to be a third assist mode.

The first assist mode may be an assist mode for a relatively weak external force compared to that of the second assist mode. For example, the first assist mode may be an assist mode for the above-described first case 310 in which the relatively weak external force is applied and the second assist mode may be an assist mode for the above-described second case 320 in which the relatively strong external force is applied. The third assist mode may be a mode that does not provide a torque for recovering balance. For example, the processor 420 may determine the assist mode to be the third assist mode when a user is to step forward because an applied external force is relatively strong. The third assist mode may be a gait assist mode. When the assist mode is determined to be the third assist mode, the processor 420 may perform operation 515 described with reference to FIG. 5.

In an example, the processor 420 determines a lateral assist mode in response to a measured roll of an upper body of the user exceeding a threshold value. For example, the lateral assist mode may be an assist mode for controlling lateral balance of the user. The lateral assist mode may include a function of each of the above-described first assist mode and the above-described second assist mode. In addition, the lateral assist mode may be used to control lateral balance of the user. The balance controlling apparatus 400 may further include an additional actuator for controlling lateral balance.

Figure 16:
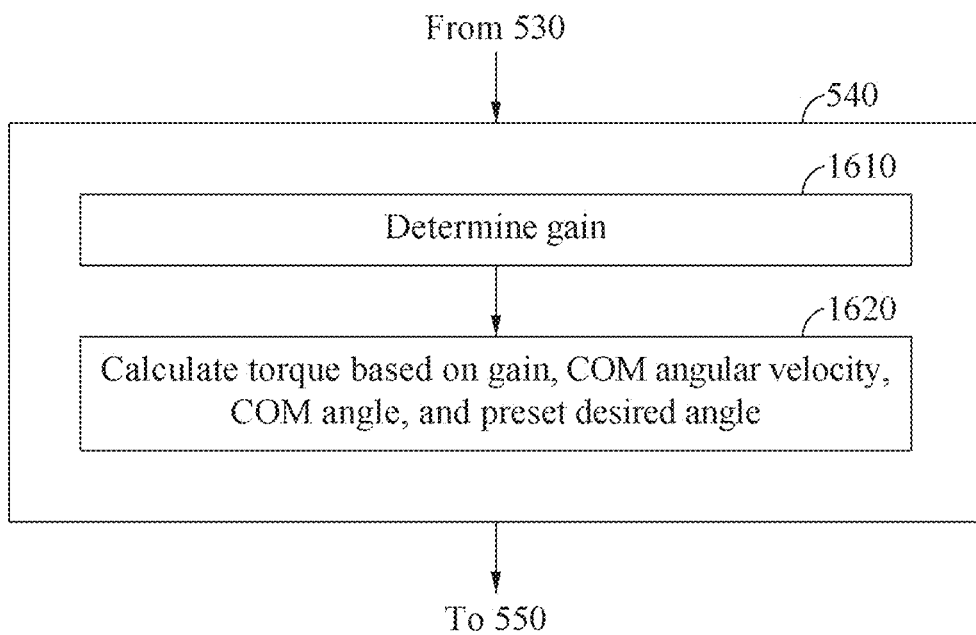
FIG. 16 is a flowchart illustrating a method of calculating a torque based on an assist mode according to at least one example embodiment.

FIG. 16 is a flowchart illustrating a method of calculating a torque based on an assist mode according to at least one example embodiment.

Referring to FIG. 16, operation 540 of calculating torque, described with reference to FIG. 5, may include operations 1610 and 1620.

In operation 1610, the processor 420 determines a gain for a determined assist mode. The processor 420 determines the gain based on at least one of a type of illness of the user, a physical condition of the user, or a desired (or, alternatively, a preset) assist method. The desired (or, alternatively the preset) assist method may be associated with a balance control degree that is selected in advance by the user.

For example, in response to the assist mode being determined to be a first assist mode, the processor 420 determines a gain for a center of mass (COM) angular velocity and a gain for a COM angle. In response to the assist mode being determined to be a second assist mode, the processor 420 determines a gain for a hip joint angular velocity, a gain for a hip joint angle, a threshold time, the gain for the COM angular velocity, and the gain for the COM angle. The threshold time may indicate a point in time at which a form of an assistance force provided in an identical assist mode is converted.

As another example, in response to the assist mode being determined to be a lateral assist mode, the processor 420 calculates a gain for a lateral assist mode. The gain for the lateral assist mode may be calculated independently of a gain of each of the first assist mode and the second assist mode.

In operation 1620, the processor 420 calculates a torque based on the determined assist mode. The processor 420 calculates the torque based on the determined gain, the calculated COM angular velocity, the calculated COM angle, and a desired (or, alternatively, a preset) angle.

For example, in response to the assist mode being determined to be the first assist mode, the processor 420 calculates the torque using Equation 5. In Equation 5, Fv1 denotes the gain for the COM angular velocity and Fp1 denotes the gain for the COM angle.

$$\text{Torque} = Fv1 \times \text{COM angular velocity} + Fp1 \times (\text{COM angle} - \text{Desired angle}) \quad \text{[Equation 5]}$$

The processor 420 may use at least one of a linear control method, a nonlinear control method, a sigmoid control method, or an exponential control method to calculate the torque for the first assist mode.

As another example, in response to the assist mode being determined to be the second assist mode, the processor 420 calculates the torque using Equation 6.

A first torque may be a torque generated before the threshold time and a second torque may be a torque generated after the threshold time. In response to the assist mode being determined to be the second assist mode, the processor 420 calculates torques in two operations based on the threshold time. Fv2 denotes the gain for the hip joint angular velocity and Fp2 denotes the gain for the hip joint angle. Fv3 denotes the gain for the COM angular velocity and Fp3 denotes the gain for the COM angle. Fv4 denotes the gain for the hip joint angular velocity and Fp4 denotes the gain for the hip joint angle. A first desired angle, a second desired angle, and a third desired angle may be set in advance.

$$\text{First torque} = Fv2 \times \text{Hip joint angular velocity} + Fp2 \times (\text{Hip joint angle} - \text{First desired angle}) \text{ for } t < t0$$

$$\text{Second torque} = Fv3 \times \text{COM angular velocity} + Fp3 \times (\text{COM angle} - \text{Second desired angle}) + Fv4 \times \text{Hip joint angular velocity} + Fp4 \times (\text{Hip joint angle} - \text{Third desired angle}) \text{ for } t > t0 \quad \text{[Equation 6]}$$

The processor 420 may use at least one of the linear control method, the nonlinear control method, the sigmoid control method, or the exponential control method to calculate the torque for the second assist mode.

Figure 17:
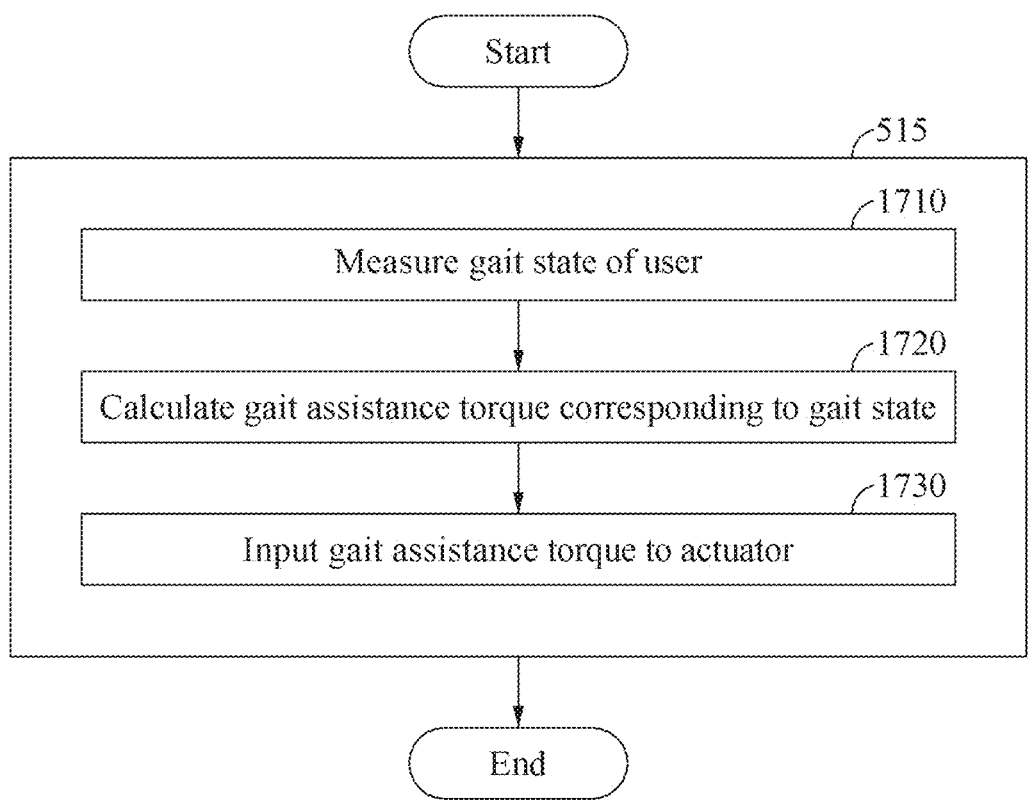
FIG. 17 is a flowchart illustrating a method of providing a gait assistance torque for a user according to at least one example embodiment.

FIG. 17 is a flowchart illustrating a method of providing a gait assistance torque for a user according to at least one example embodiment.

Referring to FIG. 17, operation 515 of performing a gait assist mode, described with reference to FIG. 5, may include operations 1710, 1720, and 1730.

In operation 1710, the processor 420 measures a gait state of a user. The processor 420 receives sensing data from at least one of sensors. The sensing data includes at least one of a hip joint angle, a hip joint angular velocity, a hip joint angular acceleration, a knee joint angle, a knee joint angular velocity, a knee joint angular acceleration, an ankle joint angle, an ankle angular velocity, an ankle angular acceleration, or inertial measurement unit (IMU) data.

For example, the processor 420 determines a gait cycle of the user based on the measured gait state. The processor 420 may determine the gait cycle corresponding to the gait state based on a desired (or, alternatively, a preset) gait profile of the user. For example, the processor 420 uses a particularly shaped adaptive oscillator (PSAO) to determine the gait cycle. As another example, the processor 420 uses a finite state machine (FSM) to determine the gait cycle. As still another example, the processor 420 uses the PSAO and the FSM to determine the gait cycle.

In operation 1720, the processor 420 calculates a gait assistance torque corresponding to the measured gait state. The processor 420 may calculate the gait assistance torque based on the determined gait cycle corresponding to the gait state. An assistance force for assisting a gait of the user may be provided by the gait assistance torque.

In operation 1730, the processor 420 inputs the calculated gait assistance torque to the actuator 430. The actuator 430 may operate based on the input gait assistance torque.

Figure 18:
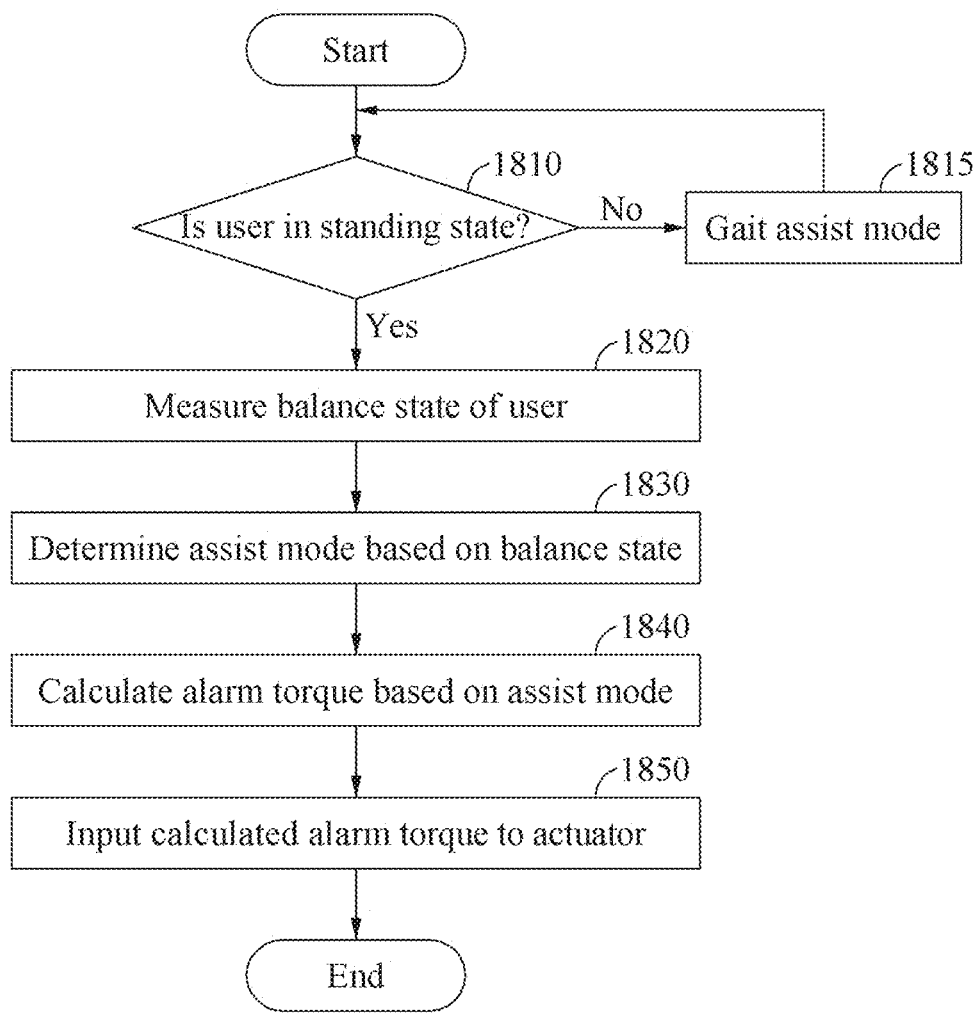
FIG. 18 is a flowchart illustrating a method of providing an alarm torque for a user according to at least one example embodiment.

FIG. 18 is a flowchart illustrating a method of providing an alarm torque for a user according to at least one example embodiment.

Referring to FIG. 18, to help the user balance, a method by which the user autonomously controls balance by self-notifying that balance needs to be controlled may be considered in addition to a method of generating a direct assistance force. For example, a patient with Charcot-Marie-Tooth (CMT) disease may be unable to recognize that there is a balance problem because a sense of an ankle is dull. In such a case, the patient may recognize a stimulus and autonomously control balance when a thigh portion having a normal sense is stimulated. Detailed description of the method by which the user autonomously controls balance by self-notifying that balance needs to be controlled will be provided through description of operations 1810, 1820, 1830, 1840, and 1850. Description of operations 1810, 1820, 1830, 1840, and 1850 may explain a method of providing biofeedback for the user.

In operation 1810, the processor 420 verifies whether the user wearing the balance controlling apparatus 400 is in a standing state. Detailed description of operation 1810 is omitted for increased clarity and conciseness because it is essentially the same as the description of operation 510 referring to FIGS. 5 and 6.

In operation 1815, the processor 420 sets an operational mode of the balance controlling apparatus 400 to be a gait assist mode. Detailed description of operation 1815 is omitted for increased clarity and conciseness because it is essentially the same as the above description of operation 515 referring to FIGS. 5 and 17.

In operation 1820, the processor measures the balance state of the user. Detailed description of operation 1820 is omitted for increased clarity and conciseness because it is essentially the same as the above description of operation 520 referring to FIGS. 5 and 7 through 14.

In operation 1830, the processor 420 determines an assist mode based on the balance state. Detailed description of operation 1830 is omitted for increased clarity and conciseness because it is essentially the same as the above description of operation 530 referring to FIGS. 5 and 15.

In operation 1840, the processor 420 calculates the alarm torque based on the determined assist mode. The alarm torque may be a torque for transmitting information including a notification that the user is controlling balance in a form of biofeedback. For example, when an upper body is to be set backward, the balance controlling apparatus 400 may operate the actuator 430 disposed on a hip joint portion to transmit information for the user to set the upper body backward.

Above-described Equations 1 through 6 may be used to calculate the alarm torque. Compared to operation 540 for calculating a torque for directly providing an assistance force, a gain calculated in operation 1840 may be smaller than a gain calculated in operation 540.

In operation 1850, the processor 420 inputs the calculated alarm torque to the actuator 430. For example, the processor 420 inputs, to the actuator 430, a value of a current or a value of a voltage corresponding to the calculated alarm torque. The actuator 430 may operate based on the input alarm torque to notify the user to self-adjust their balance.

While FIG. 18 illustrates an example embodiment in which the processor 420 calculates an alarm torque and provides the same to the user as biofeedback, example embodiments are not limited thereto. For example, in other example embodiments, the balance controlling apparatus 400 may include an output device, such as a display or speaker (not shown), and, after operation 1830, the processor 420 may provide an alert, such as an audio or visual alert, to the user to notify the user of an imbalance.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method for controlling balance of a user by a balance control apparatus worn by the user, the balance control apparatus including a controller, an actuator including a motor, and a support configured to secure to a limb of the user, the support having a first end attached to a proximal portion of the user and a second end attached to a distal portion of the user, the method comprising:
receiving, from at least one sensor of the balance control apparatus, electronic data including at least one of a hip joint angle of the user, a hip joint angular velocity of the user, a hip joint angular acceleration of the user, or inertial data associated with movement of the user;
measuring, by the controller, a balance state of the user based on the electronic data while the balance control apparatus is worn by the user such that the balance control apparatus supports the limb of the user;
calculating a torque to be generated based on the measured balance state; and
generating, by the motor of the actuator, the torque to provide a force to the support secured to the limb of the user to balance the user.

2. The method of claim 1, wherein the calculating the torque comprises:
calculating the torque for recovering balance of the user based on the measured balance state.

3. The method of claim 1, wherein the measuring comprises:
measuring the balance state based on a center of mass (COM) of the user.

4. The method of claim 3, wherein the measuring based on the COM comprises:
calculating the COM based on IMU data associated with the user and hip joint angle data, the hip joint angle data indicating the hip joint angle of the user;
calculating a COM angle based on a difference between a desired posture and a posture associated with the COM; and
calculating a COM angular velocity based on the COM angle.

5. The method of claim 4, wherein the IMU data includes a pitch of an upper body of the user.

6. The method of claim 3, wherein the measuring based on the COM comprises:
receiving ankle joint angle data, the ankle joint angle data indicating an ankle joint angle of the user;
calculating the COM based on the ankle joint angle;
calculating a COM angle based on a difference between a desired posture and a posture associated with the COM; and
calculating a COM angular velocity based on the COM angle.

7. The method of claim 6, wherein the receiving the ankle joint angle data comprises:
receiving the ankle joint angle data from an angle sensor, the angle sensor configured to attach to an ankle of the user.

8. The method of claim 1, wherein the measuring comprises:
measuring the balance state based on sole pressure data, the sole pressure data indicating a pressure applied to a sole of at least one foot of the user.

9. The method of claim 8, wherein the measuring based on the sole pressure data comprises:
receiving the sole pressure data from at least one pressure sensor, the at least one pressure sensor configured to measure pressure applied to the sole of the at least one foot of the user; and
measuring the balance state based on the pressure.

10. The method of claim 9, wherein the at least one pressure sensor includes a plurality of pressure sensors, and the measuring based on the sole pressure data comprises:
measuring the balance state based on a change in the pressure measured by the plurality of pressure sensors.

11. The method of claim 1, wherein the measuring comprises:
measuring the balance state based on a zero moment point (ZMP) of the balance control apparatus.

12. The method of claim 11, wherein the measuring based on the ZMP comprises:
calculating the ZMP based on an acceleration of an inertial measuring unit (IMU); and
measuring the balance state based on the ZMP.

13. The method of claim 1, wherein the measuring of the balance state of the user includes calculating a COM of the user based on IMU data and hip joint angle data, the hip joint angle data indicating the hip joint angle of the user, calculating a COM angle based on a difference between a desired posture and a posture associated with the COM, and calculating a COM angular velocity based on the COM angle; and the method further comprises:
determining an assist mode by,
comparing the COM angle with a plurality of threshold values to generate an angle result,
comparing the COM angular velocity with the threshold values to generate an angular velocity result, and
determining the assist mode from among a plurality of assist modes based on the angle result and the angular velocity result.

14. The method of claim 13, wherein the assist mode is one of a plurality of assist modes corresponds to different COM angular velocities.

15. The method of claim 14, wherein the calculating the torque comprises:
determining a gain; and
calculating the torque based on the gain, the COM angular velocity, the COM angle, and a desired angle.

16. The method of claim 15, wherein the gain is adjustable based on at least one of a type of illness of the user, a physical condition of the user, or an assist method.

17. The method of claim 1, wherein the measuring the balance state includes measuring a roll of an upper body of the user based on IMU data, and the method further comprises:
determining an assist mode to be a lateral assist mode, if the measured roll exceeds a threshold value.

18. The method of claim 1, further comprising:
measuring a gait state of the user, the gait state being part of a gait cycle,
wherein the calculating comprises:
calculating a torque to be generated based on the measured balance state and the gait state.

19. A balance control apparatus including a controller, an actuator including a motor, and a support configured to secure to a limb of a user, the support having a first end attached to a proximal portion of the user and a second end attached to a distal portion of the user, the balance control apparatus comprising:

the controller configured to, receive, from at least one sensor, electronic data including at least one of a hip joint angle of the user, a hip joint angular velocity of the user, a hip joint angular acceleration of the user, or inertial data associated with movement of the user, measure a balance state of the user based on the electronic data while the balance control apparatus is worn by the user such that the balance control apparatus supports the limb of the user, calculate a torque to be generated based on the measured balance state, and generate, using the motor, the torque to provide a force to the support secured to the limb of the user to balance the user.

20. A method for controlling balance of a user by a balance control apparatus worn by the user, the balance control apparatus including a controller, an actuator including a motor, and a support configured to secure to a limb of the user, the support having a first end attached to a proximal portion of the user and a second end attached to a distal portion of the user, the method comprising:

receiving, from at least one sensor of the balance control apparatus, electronic data including at least one of a hip joint angle of the user, a hip joint angular velocity of the user, a hip joint angular acceleration of the user, or inertial data associated with movement of the user;

measuring, by the controller, a balance state of the user based on the electronic data while the balance control apparatus is worn by the user such that the balance control apparatus supports the limb of the user;

calculating an alarm torque based on the balance state; and generating, by the motor of the actuator, the alarm torque as feedback to the user.

* * * * *